United States Patent
Groeschke et al.

(10) Patent No.: US 10,105,490 B2
(45) Date of Patent: Oct. 23, 2018

(54) WELDED HOUSING COMPONENTS OF A DRUG DELIVERY DEVICE

(71) Applicant: SANOFI-AVENTIS DEUTSCHLAND GMBH, Frankfurt (DE)

(72) Inventors: Jasmin Groeschke, Frankfurt am Main (DE); Hanno Juhnke, Frankfurt am Main (DE); Jan-Peter Spengler, Frankfurt am Main (DE); Hardy Kietzmann, Frankfurt am Main (DE); Matthias Scharf, Frankfurt am Main (DE); Michael Scharack, Pliezhausen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 738 days.

(21) Appl. No.: 14/361,166

(22) PCT Filed: Nov. 28, 2012

(86) PCT No.: PCT/EP2012/073796
§ 371 (c)(1),
(2) Date: May 28, 2014

(87) PCT Pub. No.: WO2013/079510
PCT Pub. Date: Jun. 6, 2013

(65) Prior Publication Data
US 2015/0112277 A1    Apr. 23, 2015

(30) Foreign Application Priority Data

Nov. 29, 2011 (EP) .................... 11191055

(51) Int. Cl.
*A61M 5/24* (2006.01)

(52) U.S. Cl.
CPC ....... *A61M 5/24* (2013.01); *A61M 2005/2485* (2013.01); *A61M 2207/00* (2013.01); *Y10T 29/4902* (2015.01)

(58) Field of Classification Search
CPC ...... A61M 2005/2485; A61M 2207/00; A61M 5/24; Y10T 29/4902
See application file for complete search history.

(56) References Cited

U.S. PATENT DOCUMENTS

| | | |
|---|---|---|
| 533,575 A | 2/1895 | Wilkens |
| 5,226,895 A | 7/1993 | Harris |
| 5,279,586 A | 1/1994 | Balkwill |

(Continued)

FOREIGN PATENT DOCUMENTS

| | | |
|---|---|---|
| EP | 0937471 A2 | 8/1999 |
| EP | 0937476 A2 | 8/1999 |

(Continued)

OTHER PUBLICATIONS

Communication pursuant to Article 94(3) EPC issued in European Patent Application No. 12794314.0 dated Dec. 11, 2017.

*Primary Examiner* — Imani Hayman
(74) *Attorney, Agent, or Firm* — McCarter & English, LLP (57) ABSTRACT

The present invention relates to a drug delivery device for dispensing a dose of a medicament, comprising: a first housing component, and a second housing component welded with the first housing component by at least one induction heatable component.

11 Claims, 10 Drawing Sheets

(56) References Cited

U.S. PATENT DOCUMENTS

| | | |
|---|---|---|
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0108195 A1 | 5/2007 | Tian et al. |
| 2009/0275916 A1 | 11/2009 | Harms et al. |
| 2012/0283660 A1* | 11/2012 | Jones ............ A61M 5/24 604/218 |

FOREIGN PATENT DOCUMENTS

| | | |
|---|---|---|
| JP | H03-129194 A | 6/1991 |
| JP | H09-290461 A | 11/1997 |
| JP | 2001-208274 A | 8/2001 |
| WO | 9938554 A1 | 8/1999 |
| WO | 0110484 A1 | 2/2001 |
| WO | 2011039226 A1 | 4/2011 |
| WO | 2011039228 A1 | 4/2011 |
| WO | 2011042538 A1 | 4/2011 |
| WO | 2011051365 A2 | 5/2011 |
| WO | 2011113868 A1 | 9/2011 |

* cited by examiner

WELDED HOUSING COMPONENTS OF A DRUG DELIVERY DEVICE

CROSS REFERENCE TO RELATED APPLICATIONS

The present application is a U.S. National Phase Application pursuant to 35 U.S.C. § 371 of International Application No. PCT/EP2012/073796 filed Nov. 28, 2012, which claims priority to European Patent Application No. 11191055.0 filed Nov. 29, 2011. The entire disclosure contents of these applications are herewith incorporated by reference into the present application.

FIELD OF INVENTION

The present invention relates to a non-releasable interconnection of housing components of a drug delivery device, such as a pen-type injector.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easily understandable. Moreover, a dose setting as well as a dose dispensing procedure must be easy to operate and has to be unambiguous.

Typically, such devices comprise a housing adapted to receive a cartridge at least partially filled with the medicament to be dispensed. The devices further comprise a drive mechanism, typically having a displaceable piston rod which is adapted to operably engage with a piston of the cartridge. By means of the drive mechanism and its piston rod, the piston of the cartridge can be displaced in a distal or dispensing direction and may therefore expel a predefined amount of the medicament via a piercing assembly which is to be releasably coupled with a distal end section of the housing of the drug delivery device.

Especially with disposable drug delivery devices, in particular with pen-type injectors, the devices are manufactured and assembled in an industrial mass-assembly process. With disposable pen-type injectors, the cartridge filled with the medicament is to be arranged inside the device, which after consumption of the medicament, is to be discarded in its entirety. During assembly of the device, the cartridge being at least partially filled with the medicament is typically assembled in a cartridge holder component, thereby forming a cartridge holder preassembly.

In a similar way, also the drive mechanism of the device to become operably engaged with the cartridge for dispensing a pre-defined dose of the medicament is arranged in a main housing- or body component in order to provide a body sub-assembly. In a final step of assembly, the cartridge holder sub-assembly and the body sub-assembly are mutually assembled and interconnected, e.g. by interconnecting body and cartridge holder. Typically, body and cartridge holder comprise mutually corresponding positive engaging locking members which may provide a non-releasable snap-in interlocking of cartridge holder and body.

Body and cartridge holder may therefore comprise mutually corresponding locking pins or respective protrusions that mate with correspondingly shaped through openings and/or recesses. Since mutually corresponding interlocking members may be comparatively filigree, interconnection of cartridge holder and body may become subject to breakage, for instance when a user unintentionally drops the device. Once, an interlocking member is broken, a stable interconnection of cartridge holder sub-assembly and body sub-assembly might be no longer given and the device in its entirety is of no longer use.

It is therefore achievable to structurally enhance and to improve the interconnection of cartridge holder and body. However, since such devices have to undergo a laborious certification and regulatory processes, usage of e.g. adhesives may have a non-negligible influence on an admission process to release the modified device into the market.

SUMMARY

It is therefore an object to the present invention to provide an improved drug delivery device featuring a robust interconnection of at least two housing components. The improvement should be implementable into existing designs of drug delivery devices and should substantially avoid application of thermal load on the cartridge and/or the medicament provided therein. Additionally, the improved interconnection should be suitable for mass-manufacturing and mass-assembly processes. The interconnection should also be implementable in a cost-efficient and highly reliable way.

The present invention relates to a drug delivery device for dispensing of a dose of a medicament. The drug delivery device comprises at least a first housing component and a second housing component welded with the first housing component by means of at least one induction heatable component. This way, first and second housing components can be bonded or welded in a non-releasable way by making use of induction welding, wherein at least one induction heatable component is in direct mechanical and thermal contact with the first and/or with the second housing component.

By applying an appropriate alternating electric field to the induction heatable component, said component will become subject to thermal heating, thereby inducing thermal energy into at least a portion of first and/or second housing component. Preferably, only such portions of first and/or second housing components become subject to induction-induced heat generation that are in direct contact with each other. Therefore, the induction heatable component is to be appropriately positioned in an interface region of first and second housing components. By means of the induction heatable component, melted portions of first and/or second housing components may evolve, by way of which the housing components can be permanently and non-releasably bonded together.

By appropriately selecting a particular induction heatable component, application of thermal energy can be spatially constricted in that area in which the induction heatable component is located. Residual portions or spatial areas of the drug delivery device may be substantially permeable and non-resonant to the alternating electric field, to which the induction heatable component is exposed. Therefore, the medicament and the cartridge can remain substantially unaffected regarding a deposition of electromagnetic or thermal energy.

In a preferred embodiment, the at least one induction heatable component is arranged in an interface section of first and second housing components. The interface section typically forms by arranging first and housing components in an at least partially mutually overlapping configuration. In such a nested configuration, at least a portion of the first housing component gets in direct contact with a corresponding surface portion of the second housing component. By arranging the at least one induction heatable component in a region, where first and second housing components mutually overlap, induction-induced thermal energy can be precisely and exclusively deposited in said interface section.

According to a further preferred embodiment, the second housing component comprises an insert portion to be assembled into a correspondingly shaped receptacle of the first housing component. Preferably, both, first and second housing components are of substantially cylindrical shape. Hence, the inner diameter of the receptacle of the first housing component matches with an outer diameter of the insert portion of the second housing component. This way, the insert portion of the second housing component, e.g. of a cartridge holder can be inserted into the corresponding receptacle of the first housing component, e.g. of a body of the drug delivery device.

Furthermore and according to another aspect, the induction heatable component is arranged in, on or below a contact surface of first and/or second housing component that gets in contact with a corresponding contact surface of second and/or first housing component when first and second housing components are arranged in a mutual assembly or pre-assembly configuration. Preferably, the contact surface of the first housing component is provided on the inside facing sidewall of the first housing component's receptacle. Accordingly, an outside facing sidewall of the insert portion of the second housing component provides a respective contact surface of the second housing component.

When in assembly configuration, the mutually corresponding contact surfaces of first and/or second housing components do not necessarily have to get in direct contact across the entire contact surface. It may be sufficient, when the contact surfaces of first and second housing components only selectively or partially get in direct contact with each other. Even in case that there exist or persist small gaps between contact surfaces of first and second housing components, which might be due to geometric or assembly tolerances, the induction induced thermal energy deposition may provide an at least partial melting of portions of first and/or second housing components to sufficiently fill the respective gap.

This way, inevitable geometric tolerances can be easily eliminated by way of the induction induced welding process.

According to a further preferred embodiment, the first and/or the second housing component comprises a receptacle to receive the induction heatable component. In particular, the first and/or second housing components may comprise a groove or a recess to receive the induction heatable component. In case of substantially cylindrically shaped housing components, such receptacle of groove may comprise a circumferential geometry in order to provide and to support a ring-like circumferential welding of first and second housing components. Accordingly, the induction heatable component may comprise a geometry and dimensions that match with the geometry of the receptacle of first and/or second housing components.

The induction heatable component may be of ring-like geometry. Moreover, it is generally conceivable, that several induction heatable components are arranged around the outer circumference of the insert portion and/or of a corresponding receptacle portion of second and/or first housing components. Then, instead of a ring-like geometry of receptacle and induction heatable component it is also conceivable to arrange several small-sized spherically or rectangularly shaped heatable components in correspondingly shaped receptacles arranged across of mutually corresponding contact surfaces of first and/or second housing components. The various induction heatable components may be spaced apart in either circumferential and/or axial direction with respect to the overall geometry of the housing components.

It is of particular benefit, when the induction heatable components assembled in a receptacle of first and/or second housing components do not protrude from the receptacle but that the induction heatable components flush with the contact surface in which the receptacle is formed.

In still another embodiment, the induction heatable component may comprise a metallic member embedded in, on or below a contact surface of first and/or second housing component. First and second housing components preferably comprise a plastic material, in particular a thermoplastic material, which is biocompatible and/or which is approved to be harmless to health. Preferably, first and second housing component comprise injection-molded plastic material, wherein the metallic member is either positively engaged with a first and/or with a second housing component or wherein the metallic member in its function as induction heatable component is directly embedded in the plastic material during an injection molding process.

Moreover and according to another embodiment, the induction heatable component may also comprise metallic particles embedded in the bulk of first and/or second housing components. Instead of or additional to a metallic member to be assembled in, on or below first and/or second housing components, metallic particles exhibiting induction-induced heating can be mixed into the plastic granules. This way, a separate step of assembling the induction heatable component with the first and/or with the second housing component may become superfluous.

In a further preferred embodiment, the induction heatable component may comprise nano-scale metallic and/or nano-scale magnetic particles. With such nano-scale metallic or magnetic particles, the plastic material, first and/or second housing components are made of may become substantially induction heatable themselves. Also here, it is intended to mix the nano-scale metallic particles and/or the nano-scale magnetic particles with the plastic granule prior to an injection molding process by way of which first and/or second housing components are manufactured.

It is of particular benefit, when the nano-scale particles are inhomogeneously dispersed within the plastic material, thereby defining a particular region in the plastic material being sensitive to electromagnetic excitation. It is also conceivable, that agglomerates of nano-scale particles serve as induction heatable component. Diameters of such aggregates can range between 100 nm and 1 µm. The nano-scale particles are preferably superparamagnetic particles and exhibit magnetic domains of the nano-scale in a range from 2 to 100 nm.

According to a further preferred embodiment, the induction heatable component comprises a laquer and/or a foil with nano-scale induction heatable particles. It is of particular benefit, when the respective laquer and/or foil covers at least a portion of a contact surface of first and/or second housing components. Hence, by providing nano-scale induction heatable particles in form of a laquer, a foil or in form of some other kinds of solid or liquid layer covering at least a portion of one of the mutually corresponding contact surfaces, sufficient induction heatable material can be arranged in the interface section of first and/or second housing component prior to a mutual assembly thereof.

By means of a laquer, a foil or by way of a comparable surface treatment of at least one of the contact surfaces, even existing and hence conventional housing components can become subject to a respective post-treatment in order to transfer applied electromagnetic energy into thermal energy.

According to another embodiment, it is further of particular benefit, when a heat generating resonance frequency of the induction heatable component lies outside a resonance frequency of water and/or outside a resonance frequency of the medicament to be dispensed by the device. Hence, the resonance frequency is shifted outside a resonant range of the medicament and its single components. This way, it can be effectively provided, that only the first and the second housing components become selectively subject to thermal treatment while the medicament and other thermally sensitive components of the drug delivery device remain substantially unaffected by the alternating electromagnetic field.

Furthermore, it is of particular benefit, to modify the resonance frequency of the induction heatable component by modifying the size of the particles, which are either to be embedded in the plastic material of the first and/or the second housing component or which are applied to the interface section of said components by a post-processing surface treatment, for instance by way of depositing a laquer and/or a foil.

In a non-limiting example, pure iron particles could serve as induction heatable components embedded in a polymer material such like Polypropylene or Polyethylene. The particle size of the iron particles could be around 0.2 mm thereby exhibiting a heat generating resonance frequency of around 4 MHz. The plastic carrier material may comprise around 15 vol.-% or 50 wt.-% of iron particles.

In another embodiment, the first and second housing component further comprise a positive interlock to at least provisionally fix the first and the second housing components, e.g. in a pre-assembly configuration. By way of a positive interlock, first and second housing components of the drug delivery device can be finally assembled or pre-assembled, thereby facilitating its general handling during the induction-induced thermal treatment.

In another embodiment, the drug delivery device is designed as a pen-type injector, wherein the first housing component comprises a body to accommodate a drive mechanism which is to become operably engaged with a piston of a cartridge. The device further comprises a second housing component designed as a cartridge holder to receive and to the fix the cartridge being at least partially filled with the medicament. By mutually assembling cartridge holder and body the drive mechanism may automatically engage with the cartridge, in particular with a piston of the cartridge. Setting and dispensing of a dose by way of the drive mechanism then repeatedly induces a distally directed displacement of a piston rod, thereby urging the piston of the cartridge in distal direction towards an injection end of the device, which is particularly provided with an injection needle.

It is of particular benefit, when the drug delivery device is designed as disposable device, wherein a cartridge at least partially filled with the medicament to be dispensed is readily arranged in the device, in particular in its cartridge holder. The cartridge may then be readily arranged inside the device when delivered to the consumer or patient.

However, the present invention is not limited to such devices but may be universally implemented with reusable devices as well. Also, the described interconnection of cartridge holder and body can be transferred to other housing components or functional components of the device that require non-releasable interconnection.

In another and independent aspect, the invention also relates to a method of assembly of a drug delivery device and in particular to a method of assembly of a pen-type injector. The method comprises the steps of providing a first sub-assembly having a first housing component, e.g. a body, and having a drive mechanism disposed therein to become operably engaged with a cartridge, e.g. filled with a medicament to be dispensed by the device. In a second step, a second sub-assembly is provided having a second housing component, e.g. a cartridge holder, and having the cartridge disposed therein which is at least partially filled with a medicament.

In a further step, first and second sub-assembly are arranged in a pre-assembly configuration in which at least a portion of the first housing component partially overlaps with a portion of the second housing component. Thereafter, in a final step of assembly, the preassembly of first and second sub-assemblies is exposed to an alternating electromagnetic field to induce thermal energy into an induction heatable component arranged in or at the first and/or second housing component. This way, thermal energy can be selectively deposited in an interface section of first and second housing components thereby inducing a non-releasable welding or bonding of first and second housing components.

It is to be noted, that all features and embodiments as described herein with respect to the drug delivery device and its various components equally apply to the method of assembly. In particular, a mentioning of a component being configured or arranged to provide a particular operation of functionality is to be understood to disclose a respective method step and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

```
H-(Lys)4-des Pro36, des Pro37
Exendin-4(1-39)-NH2,

H-(Lys)5-des Pro36, des Pro37
Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28]
Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39),
``` wherein the group -Lys6-NH2 may be bound to the C-terminus of the Exendin-4 derivative;
or an Exendin-4 derivative of the sequence

```
des Pro36 Exendin-4(1-39)-Lys6-NH2 (AVE0010),

H-(Lys)6-des Pro36 [Asp28] Exendin-4(1-39)-
Lys6-NH2, des Asp28 Pro36, Pro37, Pro38Exendin-4(1-39)-
NH2, H-(Lys)6-des Pro36, Pro38 [Asp28] Exendin-
4(1-39)-NH2, H-Asn-(Glu)5des Pro36, Pro37, Pro38 [Asp28]
Exendin-4(1-39)-NH2, des Pro36, Pro37, Pro38 [Asp28] Exendin-4(1-
39)-(Lys)6-NH2, H-(Lys)6-des Pro36, Pro37, Pro38 [Asp28]
Exendin-4(1-39)-(Lys)6-NH2, H-Asn-(Glu)5-des Pro36, Pro37, Pro38 [Asp28]
Exendin-4(1-39)-(Lys)6-NH2, H-(Lys)6-des Pro36 [Trp(O2)25, Asp28]
Exendin-4(1-39)-Lys6-NH2, H-des Asp28 Pro36, Pro37, Pro38 [Trp(O2)25]
Exendin-4(1-39)-NH2, H-(Lys)6-des Pro36, Pro37, Pro38 [Trp(O2)25,
Asp28] Exendin-4(1-39)-NH2, H-Asn-(Glu)5-des Pro36, Pro37, Pro38 [Trp(O2)25,
Asp28] Exendin-4(1-39)-NH2, des Pro36, Pro37, Pro38 [Trp(O2)25, Asp28]
Exendin-4(1-39)-(Lys)6-NH2, H-(Lys)6-des Pro36, Pro37, Pro38 [Trp(O2)25,
Asp28] Exendin-4(1-39)-(Lys)6-NH2, H-Asn-(Glu)5-des Pro36, Pro37, Pro38
[Trp(O2)25, Asp28] Exendin-4(1-39)-(Lys)6-NH2, H-(Lys)6-des Pro36 [Met(O)14, Asp28]
Exendin-4(1-39)-Lys6-NH2, des Met(O)14 Asp28 Pro36, Pro37, Pro38
Exendin-4(1-39)-NH2, H-(Lys)6-desPro36, Pro37, Pro38 [Met(O)14,
Asp28] Exendin-4(1-39)-NH2, H-Asn-(Glu)5-des Pro36, Pro37, Pro38
[Met(O)14, Asp28] Exendin-4(1-39)-NH2, des Pro36, Pro37, Pro38 [Met(O)14, Asp28]
Exendin-4(1-39)-(Lys)6-NH2, H-(Lys)6-des Pro36, Pro37, Pro38 [Met(O)14,
Asp28] Exendin-4(1-39)-(Lys)6-NH2, H-Asn-(Glu)5 des Pro36, Pro37, Pro38
[Met(O)14, Asp28] Exendin-4(1-39)-(Lys)6-NH2, H-Lys6-des Pro36 [Met(O)14, Trp(O2)25, Asp28]
Exendin-4(1-39)-Lys6-NH2, H-des Asp28 Pro36, Pro37, Pro38 [Met(O)14,
Trp(O2)25] Exendin-4(1-39)-NH2, H-(Lys)6-des Pro36, Pro37, Pro38 [Met(O)14,
```

-continued

Asp28] Exendin-4(1-39)-NH2,

H-Asn-(Glu)5-des Pro36, Pro37, Pro38
[Met(O)14, Trp(O2)25, Asp28]
Exendin-4(1-39)-NH2, des Pro36, Pro37, Pro38 [Met(O)14,
Trp(O2)25, Asp28] Exendin-4(1-39)-
(Lys)6-NH2, H-(Lys)6-des Pro36, Pro37, Pro38 [Met(O)14,
Trp(O2)25, Asp28] Exendin-4(S1-39)-
(Lys)6-NH2, H-Asn-(Glu)5-des Pro36, Pro37, Pro38
[Met(O)14, Trp(O2)25, Asp28] Exendin-
4(1 -39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in detail by making reference to the drawings in which.

DETAILED DESCRIPTION

Figure 1:
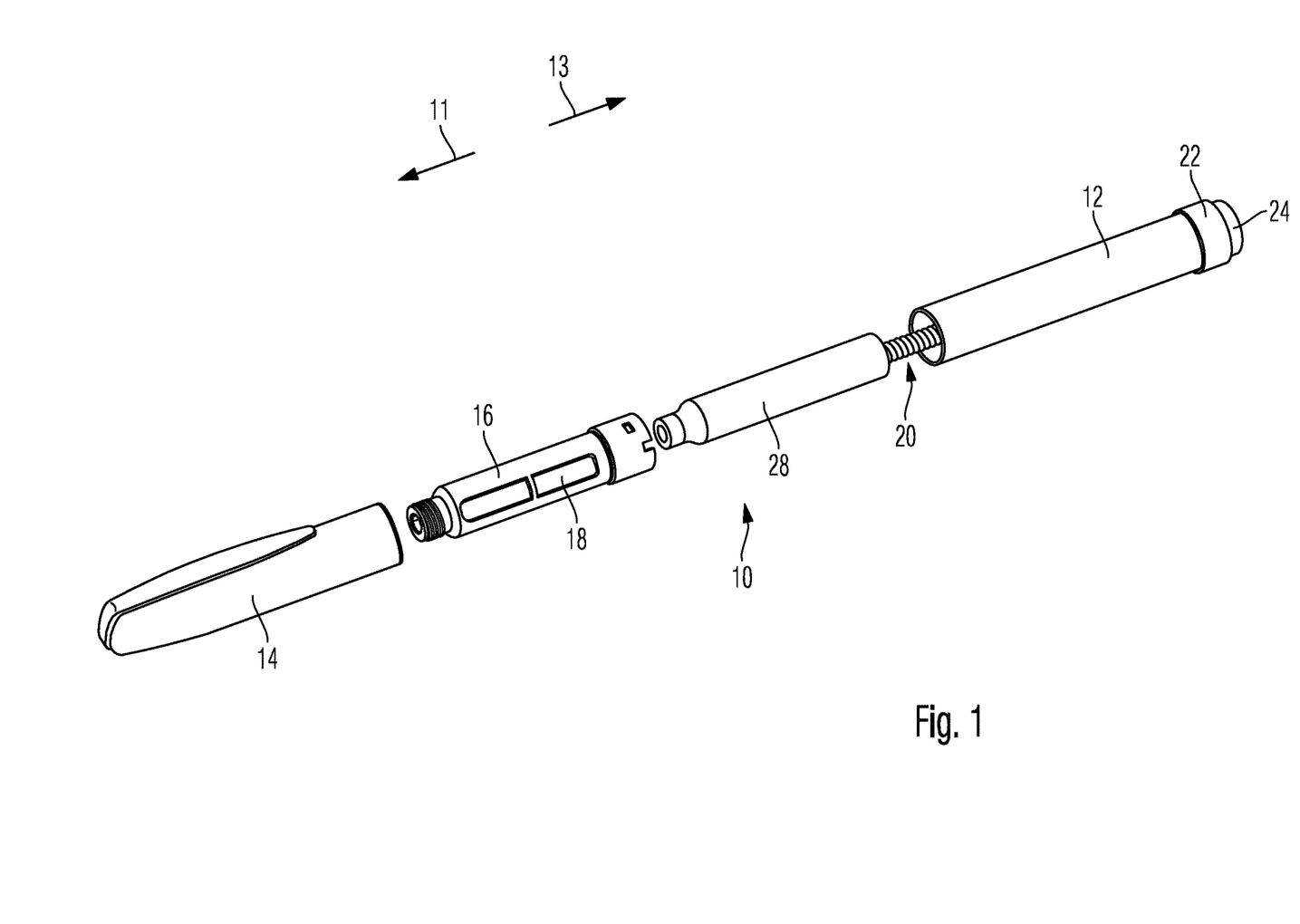
FIG. 1 shows the various components of a pen-type injector in a perspective exploded view, FIG. 2 gives an enlarged view of a cartridge holder.
Figure 2:
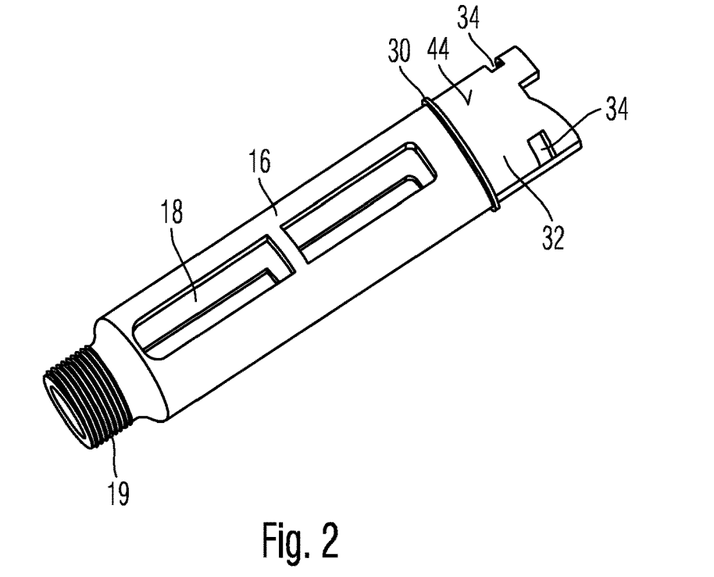
Figure 3:
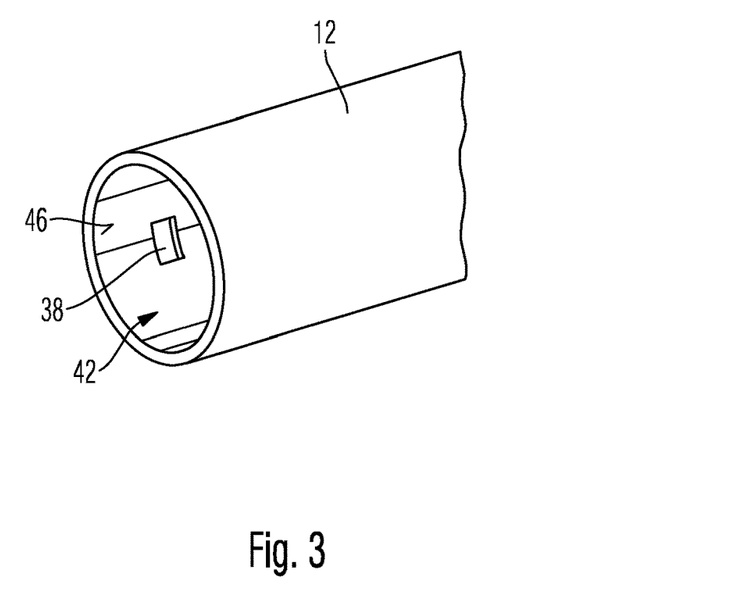
FIG. 3 shows an enlarged and perspective view of a distal end of a body.

The drug delivery device 10 as shown in FIG. 1 is designed as a pen-type injector. The device 10 comprises a body 12 of substantially tubular or cylindrical shape. At its proximal end facing towards a proximal direction 13, the body 12 features a dose dial 22 as well as a dose button 24. The body 12 which serves as a first housing component accommodates a drive mechanism which is not explicitly illustrated here. The drive mechanism comprises a series of mechanically engaging components, by way of which an actuation or manipulation of dose dial 22 and dose button 24 can be transferred in a well-defined distally directed displacement of a piston rod 20.

The piston rod 20 and in particular a pressure piece 40 arranged at a distal end thereof is adapted to operably engaged with a piston 26 of a cartridge 28, which is schematically indicated in FIGS. 4 to 10. The cartridge 28, designed as a carpule, ampoule or vial typically comprises a vitreous body confining an inner volume to receive the medicament. The cartridge 28 is assembled in a cartridge holder 16 which serves as a second housing component and which is to be non-releasably interconnected with the body 12.

The cartridge holder 16 further comprises an inspection window 18 which allows to visually inspect the filling level of the cartridge 28 disposed therein. In distal direction 11 or at its distal end the cartridge holder 16 comprises a threaded socket 19 adapted to threadedly receive a correspondingly threaded needle holder or needle hub having a double tipped injection needle. The injection needle is adapted to penetrate a pierceable septum at a distal end face of the cartridge 28. The needle further has a distally pointing end which is intended to penetrate biological tissue of a patient in order to deposit or to administer a pre-defined amount of the medicament.

The needle hub is not explicitly illustrated in the Figures and is intended to be replaced after each dose dispensing procedure took place. When not in use, the drug delivery device 10, in particular its distal needle holder 16 is intended to be protected by a protective cap 14 which can be clipped onto the needle holder 16.

Mutual assembly and interconnection of needle holder 16 and body 12 can be attained by way of a positive interlock provided by mutually corresponding and interengaging protrusions 38 extending radially inwardly from inside facing contact surface 46 of a receiving portion of the body 12 and by way of through openings or recesses 34 provided at a proximal insert portion 32 of the cartridge holder. The cartridge holder 16 comprises a circumferential rim 30 by way of which an insertion of the insert portion 32 into a distal receptacle 42 of the body 12 can be delimited. Position and geometry of protrusions 38 and recesses or through openings 34 mutually match in order to establish a non-releasable positively engaging snap-in fastening of body 12 and cartridge holder 16.

The design and mutual engagement of body 12 and cartridge holder 16 is particularly adapted for disposable drug delivery devices 10. During manufacture or assembly of the device 10, in a first step, a first sub-assembly is established by inserting and assembling the drive mechanism in the body 12. Similarly, a second sub-assembly can be prepared by assembling a pre-filled cartridge 28 in a respective cartridge holder 16. In a final assembly step, the two sub-assemblies are assembled by mutually interconnecting the cartridge holder sub-assembly and the body sub-assembly. During this final assembly step, the cartridge holder 16 is inserted with its insert portion 32 into the corresponding distally located receptacle 42 of the body 12 until protrusions 38 of the body engage with through openings or recesses 34 of the insert portion 32 of the cartridge holder 16.

Figure 4:
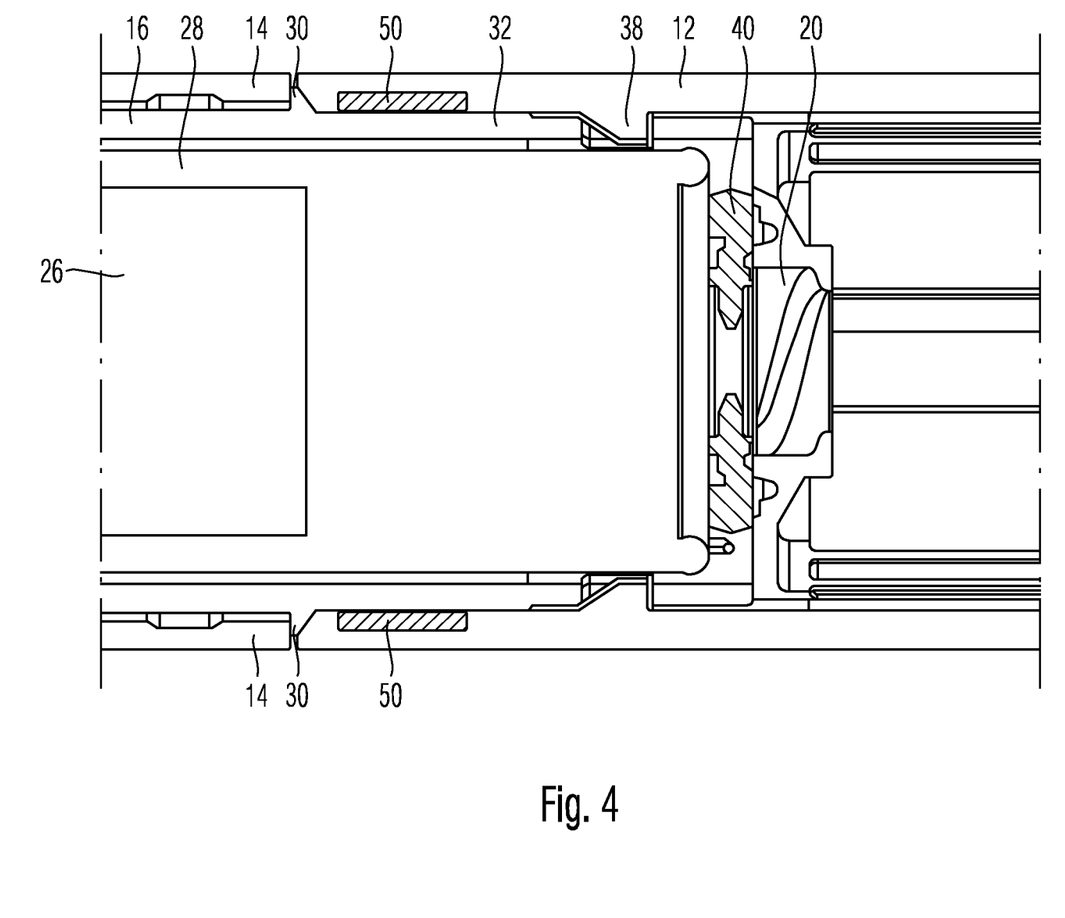
FIG. 4 shows the interface of body and cartridge holder in longitudinal cross-section with a metallic member arranged in the body receptacle.

FIG. 4 shows a cross-sectional illustration of an interface section of cartridge holder 10 and body 12 in a final assembly configuration. As becomes apparent, the radially inwardly extending protrusions 38 of the body 12 extend into corresponding recesses 34 of the insert portion 32 of the cartridge holder 16. Moreover, the circumferential and radially outwardly extending rim 30 buts against a distal front face or distal end of the body 12, thereby delimiting relative axial displacement between cartridge holder 16 and body 12 during mutual assembly. Furthermore, the distal end of the piston rod 20 and a pressure piece 40 mounted thereto and being adapted to engage with the piston 26 are shown. Moreover, a snap-in assembly of the protective cap 14 and cartridge holder 16 is indicated.

Figure 5:
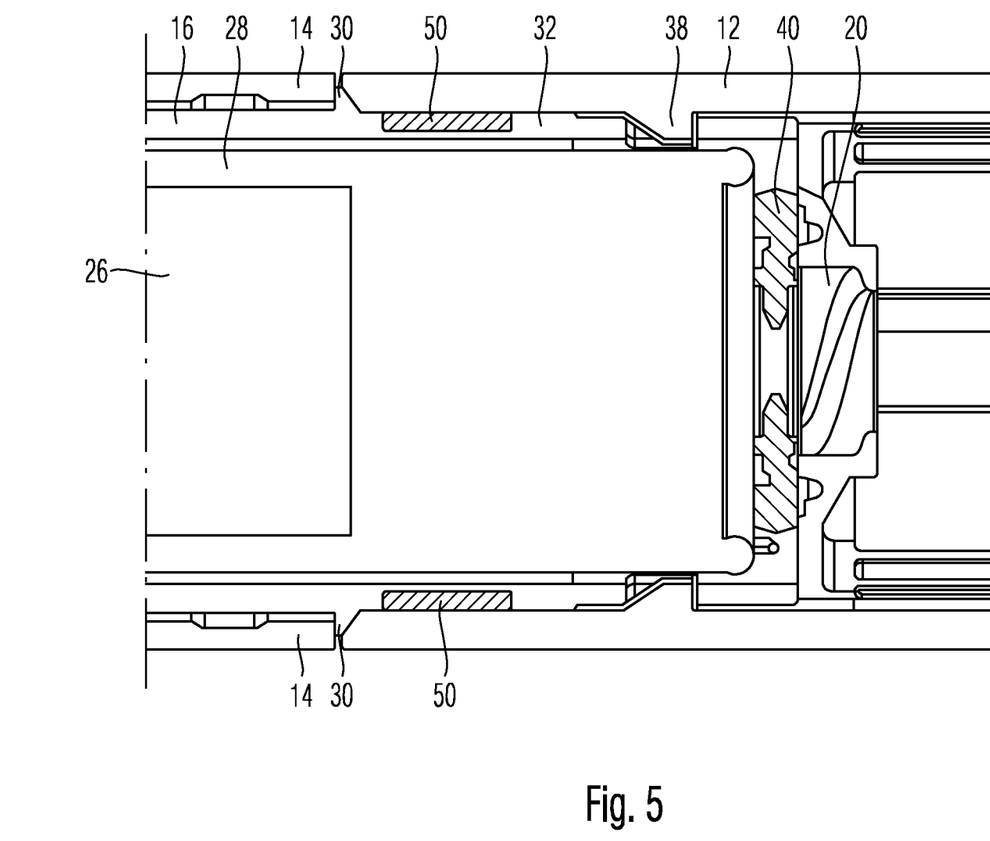
FIG. 5 shows another embodiment, wherein a metallic member is disposed in an insert portion of the cartridge holder.

As further shown in FIGS. 4 and 5, an induction heatable component 50 is provided in the interface section of cartridge holder 16 and body 12. In the configuration according to FIG. 4, the induction heatable component 50 comprises a metal ring or several metallic members which is or are embedded in the inside facing contact surface 46 of the receptacle portion of the body 12. As shown in FIG. 4, the induction heatable component 50 gets in direct contact with the outer side wall and contact surface 44 of the insert portion 32. When exposed to an appropriate alternating electromagnetic field, the induction heatable component 50 will become subject to heat development, thereby at least partially melting the injection molded components of insert portion 32 and adjacently located side wall portions of the receptacle 42 of the body 12.

In effect, insert portion 32 and body 12 of the drug delivery device 10 partially melt, fuse and consolidate. It is of particular benefit, that energy deposition into the metallic member 50 is very effective and fast, so that a mutual bonding of cartridge holder 16 and body 12 can be conducted in a rather fast and reliable way. Hence, the induction-based welding of cartridge holder 16 and body 12 is particularly suitable for an industrial mass-production or mass-assembly process. Also, a rather precise relative positioning between drug delivery device 10 and its sub-assemblies with respect to a source of electromagnetic radiation is not required. Precise deposition of thermal energy can be exclusively attained by the positioning of the induction heatable component with respect to the housing components 12, 16 that have to become subject to thermal heating.

The embodiment according to FIG. 5 differs from the one as shown in FIG. 4 in that the induction heatable component, e.g. a metallic member 50 is disposed at the outer circumference, hence in the contact surface 44 of the insert portion 32 of the cartridge holder 16. Here, in a similar way as already described with regard to FIG. 4, the induction heatable component, e.g. a ring-like or differently shaped metallic member 50 can become subject to heat treatment by means of exposure to an alternating electromagnetic field. Also here, exclusive deposition of thermal energy into the induction heatable component 50 leads to a localized and well-defined melting and fusing of the plastic material of insert portion 32 and body 12, thereby non-releasably bonding cartridge holder 16 and body 12.

While the metallic member 50 as shown in FIGS. 4 and 5 is intended to be assembled with either the body 12 or with the insert portion 32, respective housing components 12, 32 must be provided with a receptacle or with a circumferential groove adapted to receive the induction heatable component 50. The induction heatable component 50 may comprise a closed or open ring structure but may also feature several spatially and circumferentially separated ring portions to be separately assembled in corresponding receptacles provided at the inner or outer contact surface 44, 46 of body 12 or insert portion 32, respectively.

Figure 6:
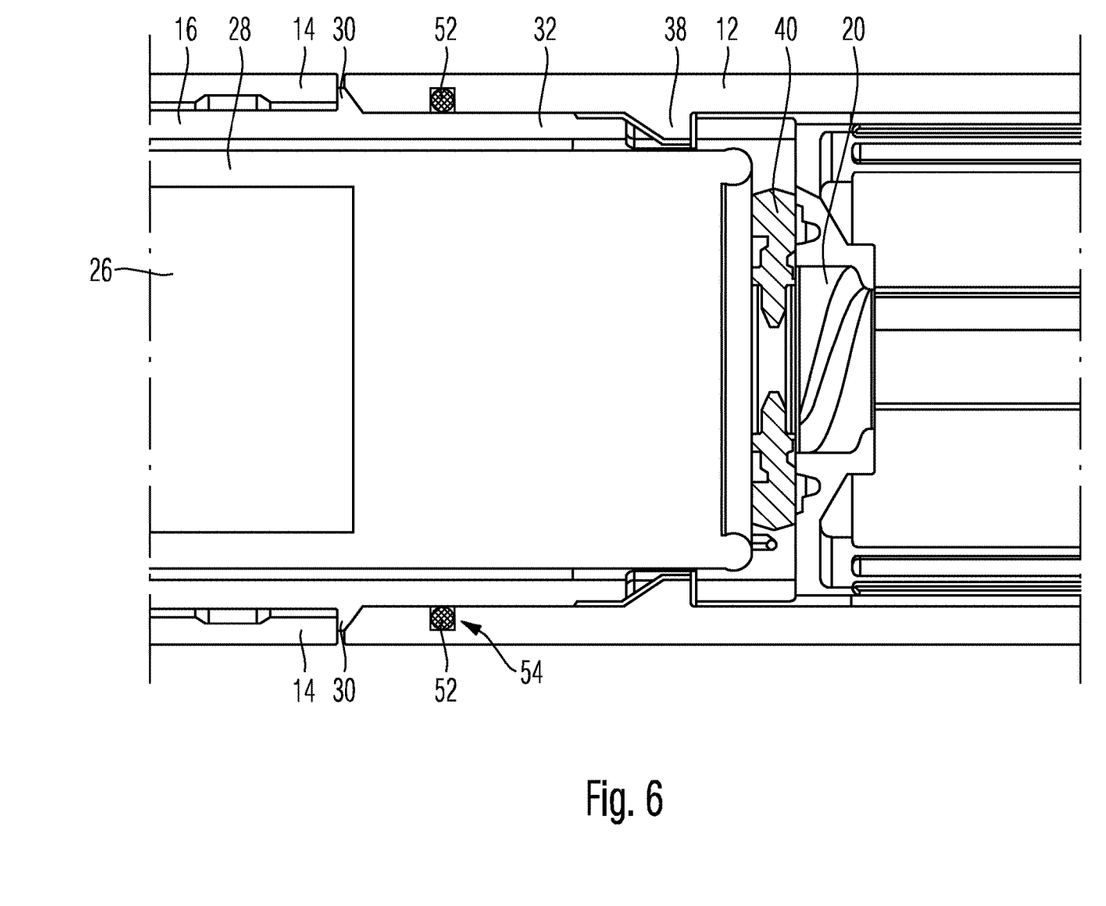
FIG. 6 shows another implementation, wherein spherically shaped metallic members are embedded in the receiving portion of the body.
Figure 7:
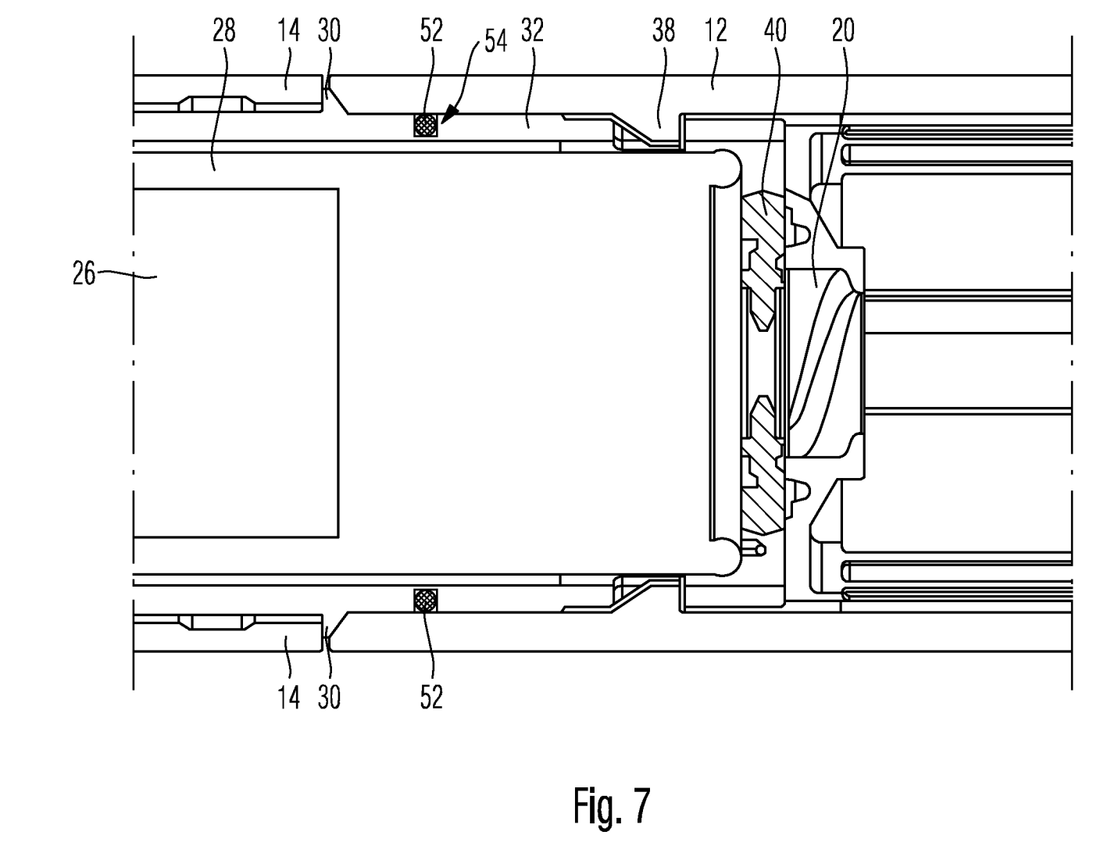
FIG. 7 shows a respective implementation of metallic members in the insert portion.

The embodiments as shown in FIGS. 6 and 7 illustrate a different approach on how to assemble an induction heatable component 52 in the interface portion of cartridge holder 16 and body 12. There, a series of spherically shaped or ball-like induction heatable components 52 are press-fitted in the comparatively soft and deformable plastic material of insert portion 32 and/or body 12. By press-fitting the spherically shaped induction heatable components 52 in interleaved portions of the housing components 16, 12, a respective receptacle 54 will be formed.

Figure 8:
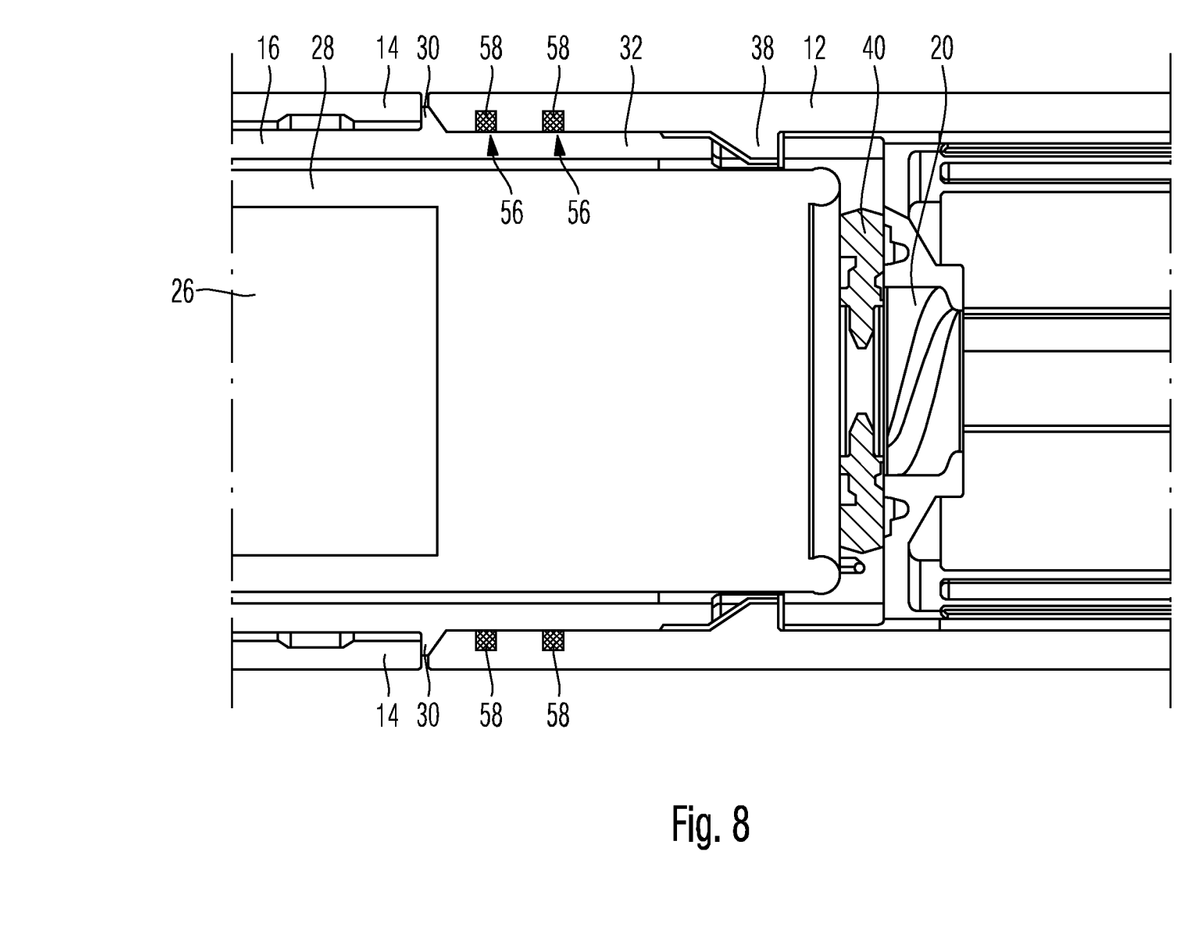
FIG. 8 shows metallic inlays in the receptacle portion and FIG. 9 shows respective metallic inlays arranged in the insert portion of the cartridge holder.
Figure 9:
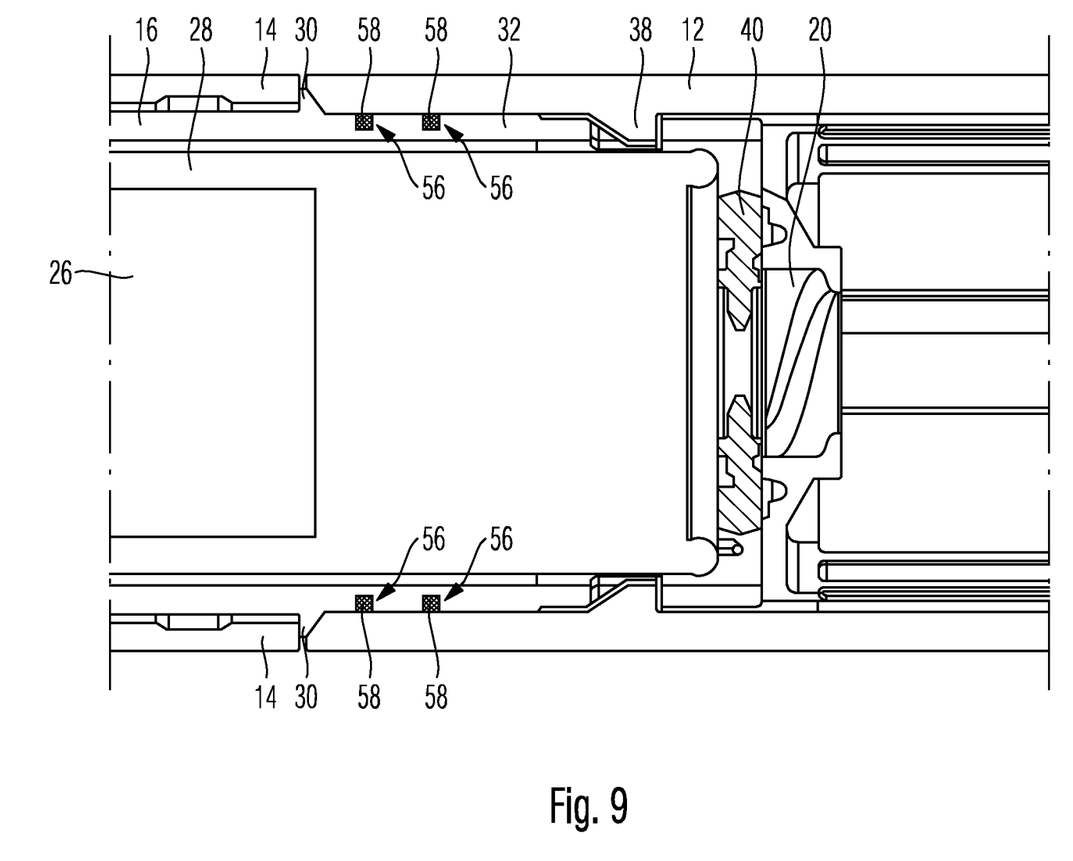

The further embodiments as shown in FIGS. 8 and 9 comprise two axially separated circumferentially extending inlays 58 arranged in a circumferentially extending groove 56, which in case of the embodiment according to FIG. 8 is provided in the inside facing side wall or contact surface 46 of the body 12 and which in case of FIG. 9 is provided at the outward facing side wall or contact surface 44 of the insert portion 32. With this embodiment, manufacture of grooves 56 can be provided by and implemented into an injection molding process by way of which cartridge holder 16 and body 12 are manufactured.

Even though the embodiments according to FIGS. 4 to 9 show at least one induction heatable component in either insert portion 32 or body 12, there are several variations and further embodiments conceivable, wherein at least one of insert portion 32 of the cartridge holder 16 and/or receptacle 42 of the body 12 are equipped with induction heatable components 50, 52, 58.

Figure 10:
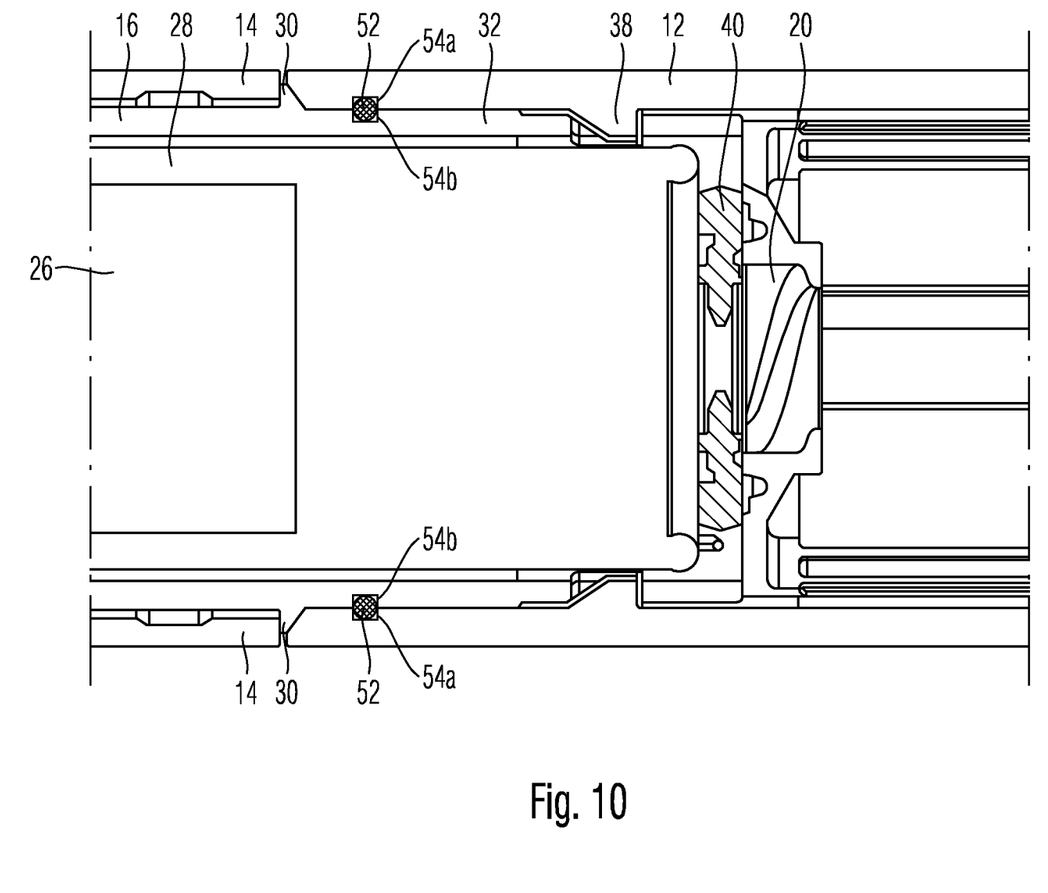
FIG. 10 is illustrative of spherical metallic members press-fitted in insert portion and receptacle.

The embodiment as illustrated in FIG. 10 can be regarded as a combination of the embodiments according to FIGS. 6 and 7 with the exception, that here, the spherical-like induction heatable components or metallic members 52 are press-fitted in the insert portion 32 in such a way, that they partially protrude from the outward facing contact surface 44 of the insert portion 32. The radially inwardly facing side wall or contact surface 46 of the body 12 comprises a correspondingly shaped recess 54a, which upon mutual assembly of cartridge holder 16 and body 12 receives the radially protruding portion of the induction heatable component 52.

This way, the induction heatable component 52 press-fitted in the insert portion 32 can provide an additional positive interlock upon insertion of the insert portion 32 into the distally located receptacle 42 of the body 12. Apart from press-fitting the induction heatable component 52 into the insert portion 32 and instead of imprinting a correspondingly shaped receptacle or indentation 54b in said insert portion 32 it is also conceivable to press-fit said inductive heatable components 52 in the inward facing side wall 46 of the body 12, thereby forming respective depressions 54a. However, the induction heatable components 52 should be press-fitted with the respective plastic components 12, 32 in such a way, that upon mutual assembly of cartridge holder 16 and body 12 the induction heatable components 52 stay and remain in the provided recess 54a, 54b.

Figure 11:
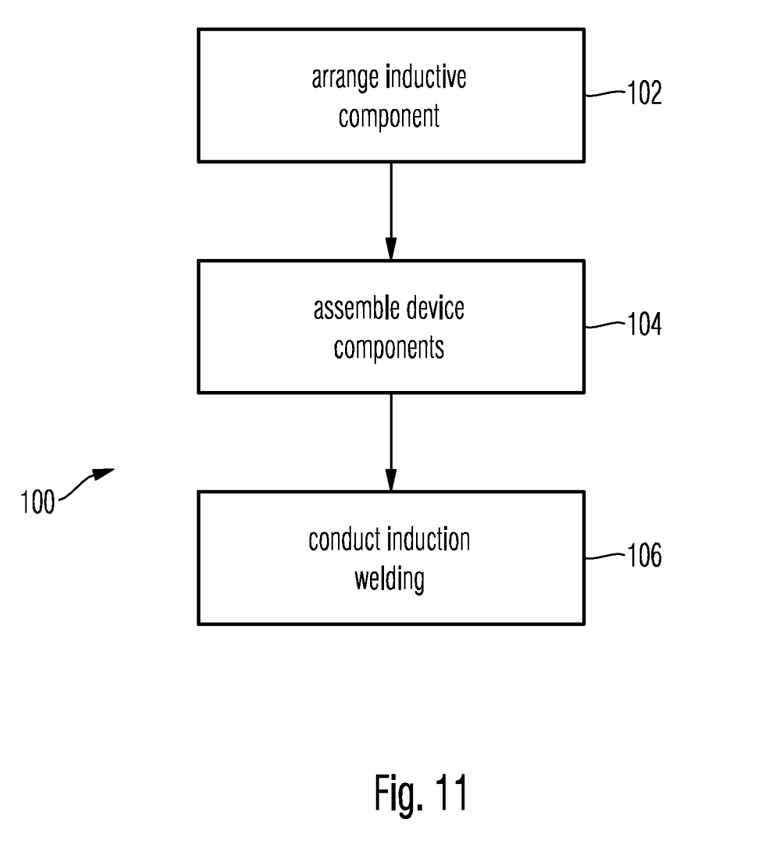
FIG. 11 shows a simplified flowchart of a method of assembly.

FIG. 11 is finally illustrative of a flowchart to illustrate the method 100 of assembling the drug delivery device 10. After providing a first and a second sub-assembly, e.g. a cartridge holder sub-assembly and a body sub-assembly, the induction heatable component or inductive component 50, 52, 58 is appropriately arranged in or on a portion of either cartridge holder 16 or body 12 in a first step 102. Preferably, the induction heatable component 50, 52, 58 is positioned in or adjacent to a contact surface 46 of insert portion 32 of the cartridge holder 16 or at a respective contact surface 44 of the body 12.

Thereafter, in step 104, the device components, cartridge holder sub-assembly and body sub-assembly are mutually assembled prior to an application of thermal energy in step 106. By way of applying an alternating electromagnetic field, an induction welding can be processed and mutual at least partial fusing and/or bonding of cartridge holder 16 and body 12 can be attained in step 106.

Even though the embodiments as depicted in FIGS. 4 to 9 are representative of induction heatable components in form of metallic members or as induction heatable components to be separately assembled with the plastic components of insert portion 32 and/or body 12, it is generally conceivable to make use of induction heatable particles in a microscopic-, mesoscopic- and/or nano-scale. Preferably, such metallic or magnetic particles can be embedded in the bulk of the plastic material, the cartridge holder 16 and/or the body 12 are made of.

Moreover, it is also conceivable, to provide a laquer and/or a foil featuring nano-scale induction heatable particles which can be separately disposed in the interface section of cartridge holder 16 and body 12 prior to their mutual assembly. Additionally, it is conceivable to modify the plastic material of cartridge holder 16 and/or body 12 in such a way, that it becomes effectively induction heatable. This can for instance be achieved by mixing nano-scale metallic and/or nano-scale magnetic particles, in particular superparamagnetic particles in the plastic granule the various housing components 12, 16 are made of.

The invention claimed is:

1. A drug delivery device for dispensing a dose of a medicament, comprising:
a first housing component comprising a body to accommodate a drive mechanism to operably engage with a piston of a cartridge at least partially filled with the medicament, and
a second housing component comprising a cartridge holder to receive the cartridge, wherein the second housing component is configured to be welded together with the first housing component by at least one induction heatable component, wherein the at least one induction heatable component is arranged in an interface section of the first housing component and the second housing component, wherein the interface section comprises a contact surface of the first housing component in contact with a corresponding contact surface of the second housing component, and
wherein each induction heatable component comprises a metallic material embedded in the contact surface and flush with the contact surface of the first housing component and/or the corresponding contact surface of the second housing component, and wherein the first housing component and the second housing component each comprise a plastic material.

2. The drug delivery device according to claim 1, wherein the second housing component further comprises an insert portion to be assembled into a receptacle of the first housing component.

3. The drug delivery device according to claim 1, wherein the first housing component and/or the second housing component comprises a receptacle to receive the at least one induction heatable component.

4. The drug delivery device according to claim 1, wherein a heat generating resonance frequency range of the induction heatable component lies outside a resonance frequency range of water and/or of the medicament to be dispensed by the device.

5. The drug delivery device according to claim 1, wherein the first housing component and the second housing component further comprise a positive interlock to at least provisionally fix together the first housing component and the second housing component.

6. The drug delivery device according to claim 1, further comprising the cartridge at least partially filled with the medicament.

7. The drug delivery device according to claim 1, wherein the metallic material comprises a plurality of metallic members embedded in the contact surface of the first housing component and/or the corresponding contact surface of the second housing component.

8. The drug delivery device according to claim 1, wherein the metallic material comprises a metal ring embedded in the contact surface of the first housing component and/or the corresponding contact surface of the second housing component.

9. The drug delivery device according to claim 1, wherein the metallic material comprises metallic particles embedded in a bulk of the first housing component and/or a bulk the second housing component.

10. A drug delivery device for dispensing a dose of a medicament, comprising:
a first housing component comprising a body to accommodate a drive mechanism to operably engage with a piston of a cartridge at least partially filed with the medicament, and
a second housing component comprising a cartridge holder to receive the cartridge, wherein the second housing component is configured to be welded together with the first housing component by at least one induction heatable component,
wherein the at least one induction heatable component is arranged in an interface section of the first housing component and the second housing component,
wherein the interface section comprises a contact surface of the first housing component in contact with a corresponding contact surface of the second housing component,
wherein the induction heatable component comprises a metallic material embedded below the contact surface of the first housing component and/or below the corresponding contact surface of the second housing component, and wherein the first housing component and the second housing component each comprise a plastic material.

11. A drug delivery device for dispensing a dose of a medicament, comprising:
a first housing component comprising a body to accommodate a drive mechanism to operably engage with a piston of a cartridge at least partially filled with the medicament, and
a second housing component comprising a cartridge holder to receive the cartridge,
wherein the second housing component is configured to be welded together with the first housing component by at least one induction heatable component, wherein the at least one induction heatable component is arranged in an interface section of the first housing component and the second housing component,
wherein the interface section comprises a contact surface of the first housing component in contact with a corresponding contact surface of the second housing component, and
wherein the at least one induction heatable component comprises metallic particles embedded in one or both of a bulk of the first housing component and a bulk of the second housing component.

* * * * *

UNITED STATES PATENT AND TRADEMARK OFFICE
CERTIFICATE OF CORRECTION

PATENT NO. : 10,105,490 B2
APPLICATION NO. : 14/361166
DATED : October 23, 2018
INVENTOR(S) : Jasmin Groeschke et al.

Page 1 of 1

It is certified that error appears in the above-identified patent and that said Letters Patent is hereby corrected as shown below:

In the Claims

At Column 16, Claim number 9, Line number 6, after "and/or a bulk", insert --of--.

At Column 16, Claim number 10, Line number 12, delete "filed" and replace with --filled--.

Signed and Sealed this
Fourteenth Day of April, 2020

Andrei Iancu
*Director of the United States Patent and Trademark Office*